US011427819B2

(12) United States Patent
Stark et al.

(10) Patent No.: US 11,427,819 B2
(45) Date of Patent: Aug. 30, 2022

(54) COEXPRESSION OF CAS9 AND TREX2 FOR TARGETED MUTAGENESIS

(71) Applicant: CITY OF HOPE, Duarte, CA (US)

(72) Inventors: Jeremy M. Stark, Duarte, CA (US); Diana Yanez, Duarte, CA (US)

(73) Assignee: CITY OF HOPE, Duarte, CA (US)

( * ) Notice: Subject to any disclaimer, the term of this patent is extended or adjusted under 35 U.S.C. 154(b) by 885 days.

(21) Appl. No.: 16/210,337

(22) Filed: Dec. 5, 2018

(65) Prior Publication Data

US 2019/0093104 A1 Mar. 28, 2019

Related U.S. Application Data

(62) Division of application No. 15/099,385, filed on Apr. 14, 2016, now Pat. No. 10,155,938.

(60) Provisional application No. 62/147,551, filed on Apr. 14, 2015.

(51) Int. Cl.
  *C12N 15/11* (2006.01)
  *C12N 9/22* (2006.01)
  *C12N 9/96* (2006.01)

(52) U.S. Cl.
  CPC ............... *C12N 15/111* (2013.01); *C12N 9/22* (2013.01); *C12N 9/96* (2013.01); *C12N 2310/20* (2017.05); *C12Y 301/00* (2013.01); *C12Y 301/11002* (2013.01)

(58) Field of Classification Search
  CPC .................. C12N 9/22; C12N 2310/20; C12Y 301/11002
  See application file for complete search history.

(56) References Cited

U.S. PATENT DOCUMENTS

2012/0276074 A1  11/2012  Scharenberg et al.
2014/0273226 A1   9/2014  Wu

FOREIGN PATENT DOCUMENTS

WO     2013/009525 A1     1/2013
WO  WO-2013126794 A1 *   8/2013  ................ A61P 7/06

OTHER PUBLICATIONS

Kabadi et al. Multiplex CRISPR/Cas9-based genome engineering from a single lentiviral vector. Nucleic Acids Research, vol. 42, No. 19, e147, Aug. 13, 2014, printed as pp. 1/11-11/11. (Year: 2014).*
Fujihara et al. CRISPR/Cas9-based genome editing in mice by single plasmid injection. Methods in Enzymology, vol. 546, pp. 319-336, 2014. (Year: 2014).*
Bennardo, N., et al., "Alternative-NHEJ is a mechanistically distinct pathway of mammalian chromosome break repair," PLoS Genet. 4(6):e1000110 (2008).
Bennardo, N., et al., "Limiting the persistence of a chromosome break diminishes its mutagenic potential," PLoS Genet. 5(10):e1000683 (2009).
Bohgaki, T., ETLA., "Genomic instability, defective spermatogenesis, immunodeficiency, and cancer in a mouse model of the RIDDLE syndrome," PLoS Genet. 7(4):e1001381 (2011).
Bouwman, P., et al., "53BP1 loss rescues BRCA1 deficiency and is associated with triple-negative and BRCA-mutated breast cancers," Nat. Struct. Mol. Biol. 17(6):688-695 (2010).
Bunting, S. F., et al., "53BP1 inhibits homologous recombination in Brca1-deficient cells by blocking resection of DNA breaks," Cell 141(2):243-254 (2010).
The Cancer Genome Atlas Research Network, "Integrated genomic analyses of ovarian carcinoma," Nature 474(7353):609-615 (2011).
Certo, M. T., et al., "Coupling endonucleases with DNA end-processing enzymes to drive gene disruption," Nat. Methods 9(10):973-975 (2012).
Cong, L., et al., "Multiplex genome engineering using CRISPR/Cas systems," Science 339(6121):819-823 (2013).
Devgan, S.S., et al., "Homozygous deficiency of ubiquitin-ligase ring-finger protein RNF168 mimics the radiosensitivity syndrome of ataxia-telangiectasia," Cell Death Differ. 18:1500-1506 (2011).
Doil, C., et al., "RNF168 binds and amplifies ubiquitin conjugates on damaged chromosomes to allow accumulation of repair proteins," Cell 136:435-446 (2009).
Evers, B., et al., "Targeting homologous recombination repair defects in cancer," Trends Pharmacol. Sci. 31:372-380 (2010).
Fradet-Turcotte, A., et al., "53BP1 is a reader of the DNA damage-induced H2A Lys15 ubiquitin mark," Nature 499(7456):50-54 (2013).
Friedland, A. E., et al., "Heritable genome editing in C. Elegans via a CRISPR-Cas9 system," Nat. Methods 10(8):741-745 (2013).
Gatti, M., et al., "A novel ubiquitin mark at the N-terminal tail of histone H2As targeted by RNF168 ubiquitin ligase," Cell Cycle 11(13):2538-2544 (2012).
Gudjonsson, T., et al., "TRIP12 and UBR5 suppress spreading of chromatin ubiquitylation at damaged chromosomes," Cell 150:697-709 (2012).
Gunn, A., et al., "Correct end use during end joining of multiple chromosomal double strand breaks is influenced by repair protein RAD50, DNA-dependent protein kinase DNA-PKcs, and transcription context," J. Biol. Chem. 286(49):42470-42482 (2011).
Gunn, A., et al., "I-Scel-based assays to examine distinct repair outcomes of mammalian chromosomal double strand breaks," Methods Mol. Biol. 920:379-391 (2012).
Hendel, A., et al., "Quantifying on- and off-target genome editing," Trends in Biotechnol. 33(2):132-140 (2015).
Huang, J., et al., "RAD18 transmits DNA damage signaling to elicit homologous recombination repair," Nat. Cell. Biol. 11(5):592-603 (2009).

(Continued)

*Primary Examiner* — Jennifer Dunston
(74) *Attorney, Agent, or Firm* — Perkins Coie LLP; Lara J. Dueppen; Yang Tang (57) ABSTRACT

A composition used in targeted mutagenesis is provided, which includes a first expression cassette comprising a nucleotide sequence which encodes a CAS9 endonuclease; a second expression cassette comprising a nucleotide sequence which encodes a guide RNA sequence, wherein the guide RNA sequence is complementary to a target genome nucleotide sequence in a cell; and a third expression cassette comprising a nucleotide sequence which encodes a Trex2 exonuclease (Trex2) gene. The first, second, and third expression cassettes may be a part or a portion of one or more expression vectors.

12 Claims, 2 Drawing Sheets
Specification includes a Sequence Listing.

(56) References Cited

OTHER PUBLICATIONS

Huen, M. S.Y., et al., "The E3 ubiquitin ligase RNF8 transduces the DNA damage signal via an ubiquitin-dependent signaling pathway," Cell 131(5):901-914 (2007).
Jinek, M., et al., "A programmable dual-RNA-guided DNA endonuclease in adaptive bacterial immunity," Science 337:816-821 (2012).
Kass, E. M., et al., "Loss of 53BP1 is a gain for BRCA1 mutant cells," Cancer Cell 17:423-425 (2010).
Kim, H., et al., "Regulation of DNA cross-link repair by the Fanconi anemia/BRCA pathway," Genes Dev. 26:1393-1408 (2012).
Kim, H., et al., "A guide to genome engineering with programmable nucleases," Nat. Rev. Genet. 15:321-334 (2014).
Kinner, A., et al., "γ-H2AX in recognition and signaling of DNA double-strand breaks in the context of chromatin," Nucl. Acids Res. 36(17):5678-5694 (2008).
Kolas, N. K., et al., "Orchestration of the DNA-damage response by the RNF8 ubiquitin ligase," Science 318(5856):1637-1640 (2007).
Leung, J. W., et al., "Nucleosome acidic patch promotes RNF168- and RING1B/BMI1-dependent H2AX and H2A ubiquitination and DNA damage signaling," PLoS Genet. 10(3):e1004178 (2014).
Lilley, C. E., et al., "A viral E3 ligase targets RNF8 and RNF168 to control histone ubiquitination and DNA damage responses," EMBO J. 29:943-955 (2010).
Lukas, J., et al., "More than just a focus: The chromatin response to DNA damage and its role in genome integrity maintenance," Nat. Cell. Biol. 13(10):1161-1169 (2011).
Mailand, N., et al., "RNF8 ubiquitylates histones at DNA double-strand breaks and promotes assembly of repair proteins,"Cell 131:887-900 (2007).
Mali, P., et al., "RNA-guided human genome engineering via Cas9," Science 339(6121):823-826 (2013).
Mattiroli, F., et al., "RNF168 ubiquitinates K13-15 on H2A/H2AXto drive DNA damage signaling," Cell 150:1182-1195 (2012).
Mattiroli, F., et al., "The nucleosome acidic patch plays a critical role in RNF168-dependent ubiquitination of histone H2A," Nat. Commun. 5:3291 (2014).
Mazur, D. J., et al., "Excision of 3' termini by the Trex1 and TREX2 3'-5' exonucleases: Characterization of the recombinant proteins," J. Biol. Chem. 276(20):17022-17029 (2001).
Moure, C. M., et al., "The crystal structure of the gene targeting homing endonuclease I-SceI reveals the origins of its target site specificity," J. Mol. Biol. 334:685-695 (2003).
Moynahan, M. E., et al., "Mitotic homologous recombination maintains genomic stability and suppresses tumorigenesis," Nat. Rev. Mol. Cell. Biol. 11(3):196-207 (2010).
Munoz, M. C., et al., "Ring finger nuclear factor RNF168 is important for defects in homologous recombination caused by loss of the breast cancer susceptibility factor BRCA1," J. Biol. Chem. 287(48):40618-40628 (2012).
Munoz, M. C., et al., "An RNF168 fragment defective for focal accumulation at DNA damage is proficient for inhibition of homologous recombination in BRCA1 deficient cells," Nucl. Acids Res. 42(12):7720-7733 (2014).
Nakada, S., et al., "RNF8 regulates assembly of RAD51 at DNA double-strand breaks in the absence of BRCA1 and 53BP1," Cancer Res. 72(19):4974-83 (2012).
Nakanishi, K., et al., "Human Fanconi anemia monoubiquitination pathway promotes homologous DNA repair," PNAS 102(4):1110-1115 (2005).
Panier, S., et al., "Tandem protein interaction modules organize the ubiquitin-dependent response to DNA double-strand breaks," Mol. Cell 47:383-395 (2012).
Panier, S., et al., "Push back to respond better: Regulatory inhibition of the DNA double-strand break response," Nat. Rev. Mol. Cell Biol. 14:661-672 (2013).
Pierce, A. J., et al., "XRCC3 promotes homology-directed repair of DNA damage in mammalian cells," Genes Dev. 13:2633-2638 (1999).
Pinato, S., et al., "RNF168, a new RING finger, MIU-containing protein that modifies chromatin by ubiquitination of histones H2A and H2AX," BMC Mol. Biol. 10:55 (2009).
Pinato, S., et al., "UMI, a novel RNF168 ubiquitin binding domain involved in the DNA damage signaling pathway," Mol. Cell. Biol. 31(1):118-126 (2011).
Porteus, M., "Strategies to increase genome editing frequencies and to facilitate the identification of edited cells," in Shondra M. Pruett-Miller (ed.), Chromosomal Mutagenesis, Methods in Molecular Biology, vol. 1239, Springer Science + Business Media New York, 2015, Nov. 3, 2014.
Ramachandrana, S., et al., "The RNF8/RNF168 ubiquitin ligase cascade facilitates class switch recombination," PNAS 107(2):809-814 (2010).
Ran, F. A., et al., "Double nicking by RNA-guided CRISPR Cas9 for enhanced genome editing specificity," Cell 154(6):1380-1389 (2013).
Ran, F. A., et al., "Genome engineering using the CRISPR-Cas9 system," Nat Protoc. 8(11):2281-2308 (2013).
Santos, M. A., et al., "Class switching and meiotic defects in mice lacking the E3 ubiquitin ligase RNF8," J. Exp. Med. 207(5):973-981 (2010).
Shanbhag, N. M., et al., "An ATM-dependent transcriptional silencing program is transmitted through chromatin in cis to DNA double strand breaks," Cell 141(6):970-981 (2010).
Shen, B., et al., "Efficient genome modification by CRISPR-Cas9 nickase with minimal off-target effects," Nat. Methods 11(4):1-32, Apr. 4, 2014, including pp. 1/32-32/32 of Supplementary Information.
Soutoglou, E., et al., "Activation of the cellular DNA damage response in the absence of DNA lesions," Science 320(5882):1507-1510 (2008).
Stark, J. M., et al., "Genetic steps of mammalian homologous repair with distinct mutagenic consequences," Mol. Cell. Biol. 24(21):9305-9316 (2004).
Stewart, G. S., et al., "The RIDDLE syndrome protein mediates a ubiquitin-dependent signaling cascade at sites of DNA damage," Cell 136:420-434 (2009).
Stewart, G. S., et al., "RIDDLE immunodeficiency syndrome is linked to defects in 53BP1-mediated DNA damage signaling," PNAS 104(43):16910-16915 (2007).
Sy, S. M.H., et al., "Critical roles of ring finger protein RNF8 in replication stress responses," J. Biol. Chem. 286(25):22355-22361 (2011).
Wang, B., et al., "Ubc13/Rnf8 ubiquitin ligases control foci formation of the Rap80/Abraxas/Brca1/Brcc36 complex in response to DNA damage," PNAS 104(52):20759-20763 (2007).
Ward, I. M., et al., "53BP1 is required for class switch recombination," J. Cell Biol. 165(4):459-464 (2004).
Xie, A., et al., "Control of sister chromatid recombination by histone H2AX," Mol. Cell. 16(6):1017-1025 (2005).
Yan, Z., et al., "A ubiquitin-binding protein FAAP20 links RNF8-mediated ubiquitination to the Fanconi anemia DNA Repair network," Mol. Cell. 47(1):61-75 (2012).

* cited by examiner

COEXPRESSION OF CAS9 AND TREX2 FOR TARGETED MUTAGENESIS

PRIORITY CLAIM

This application is a divisional of U.S. application Ser. No. 15/099,385, filed Apr. 14, 2016, which claims priority to U.S. Provisional Application No. 62/147,551, filed Apr. 14, 2015, both of which are incorporated herein by reference in their entirety, including drawings.

STATEMENT OF GOVERNMENT INTEREST

The present invention was made with government support under Grant Nos. RO1CA120954 and P30CA33572, awarded by the National Cancer Institute of the National Institutes of Health. The Government has certain rights in the invention.

SEQUENCE LISTING

This application contains a Sequence Listing, which was submitted in ASCII format via EFS-Web, and is hereby incorporated by reference in its entirety. The ASCII copy, created on Dec. 4, 2018, is named 8134US02_ST25.txt and is 7 KB in size.

BACKGROUND

Cellular genomic DNA is susceptible to damage by several factors including UV light, radiation, toxins, chemicals, viruses, oxidation, and other endogenous and environmental damage. Cells respond to this damage through processes known as the DNA damage response (DDR) that identify and correct damage to the DNA based on the type of damage inflicted. Some types of damage can be chemically reversed (e.g., methylation and covalent bonds between adjacent pyrimidine bases). In contrast, single-strand breaks (SSBs) and double-strand breaks (DSBs) require restoration of the broken phosphodiester bonds.

In SSD, only one of the two strands of DNA incurs damage, so the complementary strand can be used as a template to correct the damage using an excision repair mechanism (e.g., base excision repair (BER), and nucleotide excision repair (NER). DSB damage is repaired using an end joining (EJ) mechanism (e.g., non-homologous end joining (NHEJ) or microhomology-mediated end joining (MMEJ)); or by a homologous recombination (HR) mechanism (e.g., via homology-directed repair (HDR)). Each of these DSB repair pathways can be prone to mistakes, which can cause deletion, insertion, rearrangement, frame-shift or other mutations that can lead to malignancy or other pathologies.

DSB repair pathways show a varying propensity for genetic loss. A relatively precise form of repair is homology-directed repair (HDR) that uses the identical sister chromatid as a template for Rad51-mediated strand invasion and nascent DNA synthesis. In contrast, EJ pathways are variably mutagenic, depending on the extent of end-processing and the fidelity of end-pairing. For instance, EJ via the NHEJ machinery used during V(D)J recombination (classical NHEJ) has the potential to be precise. However, if DSB ends are not readily ligated without prior significant processing (e.g., degradation of damaged bases or protruding single stranded DNA at the ends), such classical NHEJ can lead to deletion and/or insertion mutations. Furthermore, Ku-independent EJ (Alternative-NHEJ, Alt-NHEJ) often leads to deletion or insertion mutations, which are predominantly associated with short stretches of homology (microhomology) at repair junctions. Similar to Alt-NHEJ is the single-strand annealing (SSA) pathway of homologous recombination, which also causes deletions with homology at repair junctions, but involves extensive regions of homology. In addition, for each of these pathways, loss of correct end-pairing during the repair of multiple simultaneous DSBs can lead to chromosomal rearrangements. For instance, EJ between distal ends of two tandem DSBs (Distal-EJ) results in loss of the chromosomal segment between the DSBs.

The factors and pathways that influence DSB repair may be exploited for the purpose of developing experimental and therapeutic systems in a wide range of species. These systems may be used for various functions, such as to study gene function in plants and animals, to engineer transgenic cells and organisms, or to develop therapeutic interventions such as in vivo or ex vivo gene therapy in subjects with chromosomal aberrations or aberrantly expressed gene products. However, because these pathways are prone to cause different mutagenic outcomes, it is desired to develop systems that influence the DSB repair machinery to enhance the frequency of the desired outcome.

SUMMARY

In certain embodiments, a composition is provided. The composition may include a first expression cassette comprising a nucleotide sequence which encodes a CAS9 endonuclease; a second expression cassette comprising a nucleotide sequence which encodes a guide RNA sequence, wherein the guide RNA sequence is complementary to a target genome nucleotide sequence in a cell; and a third expression cassette comprising a nucleotide sequence which encodes a Trex2 exonuclease (Trex2) gene. In some embodiments, the first, second, and third expression cassettes comprise a portion of one or more expression vectors.

In certain embodiments, a system for disrupting a target nucleotide sequence in a cell is provided. The system may include a CAS9 endonuclease; a guide RNA sequence, wherein the guide RNA sequence is complementary to the target genomic nucleotide sequence; and a Trex2 exonuclease. In some embodiments, the CAS9 endonuclease, the guide RNA sequence, and the Trex2 exonuclease are coexpressed in the cell by one or more expression vectors.

In certain embodiments, a method for disrupting a target genomic nucleotide sequence in a cell is provided. Such methods may include a step of transfecting the cell with an effective amount of a composition that includes a first expression cassette comprising a nucleotide sequence which encodes a CAS9 endonuclease; a second expression cassette comprising a nucleotide sequence which encodes a guide RNA sequence, wherein the guide RNA sequence is complementary to a target genome nucleotide sequence in a cell; and a third expression cassette comprising a nucleotide sequence which encodes a Trex2 exonuclease. In some embodiments, transfection of the composition results in a disruption of the target genomic nucleotide sequence, and wherein the disruption is caused by an insertion or deletion of one or more nucleotides within the target genome nucleotide sequence.

BRIEF DESCRIPTION OF THE DRAWINGS

FIG. 1A. Shown are diagrams of the DR-GFP and EJ5-GFP reporters for measuring HDR and Distal-EJ, respectively. Also shown are guide RNA (gRNA) targeting sequences used for inducing chromosomal breaks with the gRNA/CAS9 system (see the lines below the italicized sequence labeled gDR, gEJ5-5, and gEJ5-3), where the targeted cleavage site is three nucleotides upstream from the 3' end of the gRNA. Since the gRNAs include sequences flanking the I-SceI recognition site, each gRNA targets a unique site on the reporters. The I-SceI recognition site is in lower case. FIG. 1B. Repair events induced by I-SceI, CAS9-WT, and CAS9-D10A. The expression cassettes for the gRNAs and CAS9 are present on the same plasmid. U2OS cells with the DR-GFP and EJ5-GFP reporters were transfected with a set of gRNA/CAS9 plasm ids, as well as I-SceI, or left untransfected. Shown are representative flow cytometry plots (FL1/green on the Y-axis, FL2 on the X-axis) from these transfections, with the GFP+ population delineated in the upper gate, used to determine the mean frequencies of GFP+ cells (N=3). FIG. 1C. CAS9-WT is proficient at inducing loss of the I-SceI site via mutagenic Proximal-EJ, which is further increased with co-expression of the exonuclease Trex2. U2OS cells with the EJ5-GFP reporter were transfected with I-SceI and CAS9-WT as in B, except including either the Trex2 expression vector or empty vector (EV). Shown are representative amplification products from these transfections digested with the I-SceI endonuclease, which were used to determine the frequency of I-SceI site loss (N=6, *p<0.03). Also shown is the frequency of Distal-EJ from the transfections of CAS9-WT with or without Trex2 (*p<0.0001).

DETAILED DESCRIPTION

Expression systems, vectors and plasmids for use in targeted mutagenesis are provided herein. Targeted mutagenesis, or targeted genetic engineering allows one to introduce targeted, tailored changes in a mammalian genome for therapeutic or research purposes. Such changes may include the insertion, disruption, deletion, or replacement of a genomic sequence at a predetermined locus or target genomic nucleotide sequence.

Upon damage by endogenous or exogenous factors, DNA is repaired by several proteins and factors that make up the DNA damage response. These repair mechanisms can be harnessed and exploited in genetic engineering methods used in research and treatment of pathologies and malignancies that are dependent and/or susceptible to mutations resulting from the DNA repair process. Therefore, according to the embodiments described herein, compositions that may be used in methods for inducing a targeted mutagenesis event are provided.

In certain embodiments, a composition that may be used to transfect cells in accordance with the methods described herein is provided. The composition may include one or more expression cassettes that, when inserted into an expression vector, express an endonuclease (or endonuclease system) and an exonuclease.

Many endonucleases (e.g., TALENs, I-SceI, Zinc Fingers, etc.) are associated with a protein targeting agent that guides the endonuclease to specifically bind a target DNA sequence at a predetermined or fixed locus on a mammalian gene or genome (e.g., a human, mouse, rat, rabbit, canine, porcine, bovine, or other mammalian gene or genome). However, customizing such endonucleases to cut the gene or genome at a designated target site requires major protein engineering efforts. Thus, the embodiments described herein use an RNA-guided DNA endonuclease—CAS9 of the type II (clustered regularly interspaced short palindromic repeat) CRISPR—Cas—which includes a guide RNA sequence (gRNA) as a targeting agent to locate a target DNA sequence and the CAS9 protein to cut DNA. This programmability of the CAS9 endonuclease using customizable RNAs brings flexibility and versatility for targeted genome modification and other methods described herein. In contrast to meganucleases and TALENs, CAS9 generates blunt ended double strand breaks. Using a CAS9 system (ADDGENE; #42230, pX330, Zhang lab), it is shown in the Examples below that co-expression of Trex2 can promote elevated mutagenesis at CAS9 targeted chromosomal breaks. It is also shown below that co-expression of Trex2 can limit the frequency of rearrangements caused by joining together DSB ends from multiple different CAS9 targeted chromosomal DSBs, specifically a deletion rearrangement caused by distal EJ between two tandem DSBs. Accordingly, use of CAS9 in concert with Trex2 has significant biotechnological and therapeutic potential to cause efficient mutagenesis at specific predetermined cleavage sites.

Therefore, in certain embodiments, the endonuclease system is a CRISPR/CAS9 system and the exonuclease is Trex2. In these embodiments, the composition includes (i) a first expression cassette that includes a nucleotide sequence that encodes a CAS9 endonuclease, (ii) a second expression cassette that that includes a nucleotide sequence that encodes a guide RNA sequence designed to be complementary to a target genomic nucleotide sequence in a cell, and (iii) a third expression cassette that includes a nucleotide sequence that encodes a Trex2 exonuclease. Each of the first, second and third expression cassettes include a promoter sequence selected from those known in the art which determines the species specificity of the system expressed by the expression vector.

In one embodiment, the first, second and third expression cassettes may be inserted into one or more expression vectors for delivery to a cell, a population of cells, or a subject.

In certain embodiments, the first and second expression cassettes may be inserted into a first expression vector, and the third expression vector is inserted into a second expression vector. In other embodiments, the first, second and third expression cassettes are inserted into a single expression vector. In still other embodiments, the first expression cassette is inserted into a first expression vector, the second expression cassette is inserted into a second expression vector, and the third expression cassette is inserted into a third expression vector. In this embodiment, each expression cassette is expressed by a separate expression vector.

In certain other embodiments, a system for disrupting or otherwise modifying or editing a target nucleotide sequence in a cell is provided. The system may include a CAS9 endonuclease, a guide RNA sequence that is complementary to a target genomic nucleotide sequence, and a Trex2 exonuclease. In some aspects, the CAS9 endonuclease, the guide RNA sequence, and the Trex2 exonuclease are coexpressed in the cell by one or more expression vectors. In some aspects, the systems described herein are expressed by a cell that is transfected with the composition described above.

A CAS9 endonuclease used in the systems described herein and/or are encoded by the nucleotide sequence of the first expression cassette of the composition above may be a wild type CAS9 (CAS9-WT), or may be any variant thereof that is suitable for inducing mutagenesis at a predetermined target sequence (e.g., CAS9 (D10A), single Nickase or Double Nickase). The two functional domains of CAS9, RuvC and HNH, each cut a DNA strand in a double-stranded DNA molecule. As such, when both domains are active, a double stranded bread (DSB) is induced by CAS9. This DSB may be repaired by the Non-Homologous End Joining (NHEJ) repair pathway or a homology directed repair (HDR) mechanism.

In certain embodiments, the compositions and systems described herein may be used to enhance the efficiency of the NHEJ repair pathway, resulting in an insertion or deletion (also referred to herein as "InDel") of one or more nucleotides in the genomic DNA at the DSB site. These InDels alter the open reading frame (ORF) of a target genomic nucleotide sequence, thereby disrupting the target genomic nucleotide sequence by changing the amino acid sequence downstream of the DSB, introducing a premature stop codon at the DSB, or by shifting the reading frame to create a stop codon downstream of the DSB. This disruption can be exploited therapeutically to decrease or eliminate expression of an aberrantly expressed gene that is associated with a disease, such as an oncogene or the like.

The guide RNA sequence is designed so as to bind or hybridize to a target genomic nucleotide sequence in a target cell. To design the guide RNA sequence, a target sequence is selected on either strand of the double stranded DNA, and includes an appropriate protospacer adjacent motif (PAM) sequence in the genomic DNA. The PAM sequence allows the CAS9 component to bind and cut the target DNA sequence that is bound by the guide RNA sequence. A PAM sequence is selected based on the species of bacteria that the CAS9 was derived. In some embodiments, the PAM sequence is derived from *S. pyogenes* (NGG; SEQ ID NO:1); *N. meningitides* (NNNNGATT; SEQ ID NO:2); *S. thermophiles* (NNAGAA; SEQ ID NO:3); *T. denticola* (NAAAAC; SEQ ID NO:4) or any other suitable sequence.

The target sequence may be of any suitable length. In certain embodiments, the target sequence is approximately 20 nucleotides in length (not including the PAM sequence). In other embodiments, the target sequence is approximately 10, 11, 12, 13, 14, 15, 16, 17, 18, 19, 20, 21, 22, 23, 24, 25, 26, 27, 28, 29, or 30 nucleotides in length (not including the PAM sequence). In some embodiments, the target sequence is less than 10 nucleotides in length or is more than 30 nucleotides in length (not including the PAM sequence).

Once the target sequence is selected, the guide RNA sequence may be designed by any suitable method known in the art for designing complementary nucleotide sequences. In some embodiments, the target sequence and/or guide RNA sequence may be selected and/or designed using a bioinformatics program. Examples of software programs that are suitable for designing the target and/or guide RNA sequences include, but are not limited to, Feng Zhang lab's Target Finder, Michael Boutros lab's Target Finder (E-CRISP), CRISPRdirect, sgRNAcas9, Broad Institute CRISPR Design Tool, GenScript gRNA design tool, OMICtools CRISPR gRNA design tool, ZiFiT Targeter, E-CRISP, Cas-OFFinder, CasFinder, CRISPR Optimal Target Finder, or any other programs known in the art.

To ensure that a target gene is sufficiently disrupted, a target sequence should be chosen within the first or second exon of the gene, or otherwise sufficiently near the N-terminus of the coding region of the gene.

In certain embodiments, the compositions and systems may be transfected into one or more cells using any suitable expression vector which delivers the composition to the cell or cells. Any suitable expression vectors may be used in accordance with the embodiments described herein including, but not limited to, plasmids and recombinant viral vectors. Suitable viruses that may be used to design a recombinant viral vector for use in the embodiments described herein include, but are not limited to, adeno-associated virus (AAV), adenovirus, lentivirus, or baculovirus.

In some embodiments, the expression vector is a plasmid. In such embodiments, the composition described herein may include a first plasmid that, when delivered to a cell, expresses the CRISPR system components, CAS9 and the guide RNA sequence; and a second plasmid that, when delivered to a cell with the first plasmid, coexpresses Trex2. Alternatively, the composition may include a plasmid that expresses all three expression cassettes, or may include three plasmids, the first of which expresses the CAS9, the second of which expresses the guide RNA sequence, and the third of which expresses the Trex2.

According to some embodiments, the compositions and systems described herein may be used in methods to disrupt a target genomic nucleotide sequence in a cell. Such methods may include transfecting a cell with an effective amount of a composition that includes one or more expression cassettes that, when inserted into an expression vector, express an endonuclease (or endonuclease system) and an exonuclease. In certain embodiments, the endonuclease system is a CRISPR system and the exonuclease is Trex2. In these embodiments, the composition includes (i) a first expression cassette that includes a nucleotide sequence that encodes a CAS9 endonuclease, (ii) a second expression cassette that that includes a nucleotide sequence that encodes a guide RNA sequence designed to be complementary to a target genomic nucleotide sequence in a cell, and (iii) a third expression cassette that includes a nucleotide sequence that encodes a Trex2 exonuclease. The disruption that results from the transfection of the composition may be caused by an insertion or a deletion of one or more nucleotides within the target genome nucleotide sequences.

In some embodiments, the cells transfected with the compositions or systems described herein may be transfected in vitro. In such embodiments, the methods which use the compositions and systems described above may be used in genetic engineering research on a cellular level to investigate the consequences of DNA mutations (e.g., deletions, insertions, disruptions or replacements) that are caused by mistakes in the DNA repair process. To understand the repair of chromosomal breaks in mammalian cells, targeted chromosomal breaks are generated in cell lines, and the repair products that arise from these DNA breaks are subsequently evaluated.

In other embodiments, the cells transfected with the compositions or systems described herein may be transfected in vivo or ex vivo. In such embodiments, the methods which use the compositions and systems described above may be used in genetic engineering or gene therapy research or treatment on an organismal level. For example, the compositions, systems, and methods described herein may be used to generate knock-out animals which lack a particular gene, or may be used to treat a population or sub population of cells obtained from a subject suffering from a disease which is associated with overexpression or other dysfunction of a target gene product. In such a method, the composition and systems described herein may be used to disrupt the target gene product in the subject's cells (e.g., to reduce expression of the gene product) in order to treat or otherwise ameliorate symptoms of the subject's disease.

Many endonucleases (e.g., TALENs, I-SceI, Zinc Fingers, etc.) are associated with a protein targeting agent that guides the endonuclease to specifically bind a target DNA sequence at a predetermined or fixed locus on a mammalian gene or genome (e.g., a human, mouse, rat, rabbit, canine, porcine, bovine, or other mammalian gene or genome). However, customizing such endonucleases to cut the gene or genome at a designated target site requires major protein engineering efforts. Thus, the embodiments described herein use an RNA-guided DNA endonuclease—CAS9 of the type II (clustered regularly interspaced short palindromic repeat) CRISPR—Cas—which includes a guide RNA sequence (gRNA) as a targeting agent to locate a target DNA sequence and the CAS9 protein to cut DNA. This programmability of the CAS9 endonuclease using customizable RNAs brings flexibility and versatility for targeted genome modification and other methods described herein. In contrast to meganucleases and TALENs, CAS9 generates blunt ended double strand breaks. Using a CAS9 system (ADDGENE; #42230, pX330, Zhang lab), it is shown in the Examples below that co-expression of Trex2 can promote elevated mutagenesis at CAS9 targeted chromosomal breaks. It is also shown below that co-expression of Trex2 can limit the frequency of rearrangements caused by joining together DSB ends from multiple different CAS9 targeted chromosomal DSBs, specifically a deletion rearrangement caused by distal EJ between two tandem DSBs. Accordingly, use of CAS9 in concert with Trex2 has significant biotechnological and therapeutic potential to cause efficient mutagenesis at specific predetermined cleavage sites.

In certain embodiments, transfection or delivery of the expression vectors (e.g., plasmids) may be accomplished by any suitable method known in the art including, but not limited to, viral transfection or transduction, microinjection, electroporation, sonoporation, optical transfection, impalefection, hydrodynamic delivery, nucleofection, lipofection, dendrimeric transfection, magnetofection, gene gun transfection, nano particle-based transfection, calcium phosphate transfection, viral transfection, and cell squeezing.

The following examples are intended to illustrate various embodiments of the invention. As such, the specific embodiments discussed are not to be construed as limitations on the scope of the invention. It will be apparent to one skilled in the art that various equivalents, changes, and modifications may be made without departing from the scope of invention, and it is understood that such equivalent embodiments are to be included herein. Further, all references cited in the disclosure are hereby incorporated by reference in their entirety, as if fully set forth herein.

EXAMPLES

Example 1: Coexpression of CAS9 and Trex2 Enhances Gene Disruption of a Target Nucleotide Sequence Materials and Methods Cell lines and plasmids. U2OS cells harboring the DR-GFP and EJ5-GFP reporters were generated as previously described (26, 27).

CAS9 vectors. The gRNA/CAS9 plasm ids were generated from pX330 (CAS9-WT version) and pX335 (CAS9-D10A version), which were generously deposited to ADDGENE (42230, and 42335, respectively) by Dr. Feng Zhang (30). To generate the guide RNA expression cassettes, targeting sequences shown in FIGS. 1A-C were introduced into the Bbs1 site in these plasm ids.

Trex vectors. The Trex2 vector was made as previously described (Bennardo et al. 2009 PLoS Genetics, which is hereby incorporated by reference). Briefly, the mouse Trex2 coding sequence is present within a single exon, and thus was generated from PCR amplification of mouse ES genomic DNA for cloning into pCAGGS-BSKX, using the following primer sequences: 5'cagctctaggcctcattgtt (SEQ ID NO:5) and 5'agagcctggatgaatggatg (SEQ ID NO:6).

Transfections and DSB reporter assays. To characterize the gRNA/CAS9 plasmids in comparison with I-Scel (i.e. FIGS. 1A-C), 0.4 µg total plasmid was transfected with 1.8 µL LIPOFECTAMINE® 2000 (a transfection reagent) in 0.6 m L. The percentage of GFP+ cells was determined by FACS analysis (CYAN ADP, Dako) three days after transfection. For comparison, the repair value for each transfection is often divided by the mean repair value for the parallel control transfection (i.e., siCTRL and/or EV). Each repair value is the mean of at least three independent transfections, error bars reflect the standard deviation, and statistics were performed with the unpaired t-test. Error bars denote the standard deviation from the mean.

Results

Examining repair of chromosomal breaks induced by distinct site-specific nucleases. Several systems were developed to evaluate HR induced by a distinct set of site-specific nucleases: I-Scel, CAS9-WT, and CAS9-D10A. I-Scel is a yeast homing endonuclease that induces a double strand break (DSB) within an 18 bp sequence, causing 4 nt overhangs (31). The CAS9 nuclease system is derived from an *S. pyogenes* immune response pathway that uses a guide RNA (gRNA) to target strand breaks in homologous DNA (32, 33). Expression of this nuclease has been adapted to mammalian cells in a single plasmid containing two expression cassettes: one for the protein CAS9, and one for a synthetic gRNA with the target sequence at the 5' end (32). CAS9 contains two nuclease domains that induce a blunt ended DSB that is positioned 3 nt upstream of the 3' end of the target sequence (32, 33). The CAS9-D10A mutation disrupts the N-terminal nuclease domain, such that CAS9-D10A is proficient at nicking the DNA strand complementary to the gRNA, but is deficient at cleaving the second strand (32, 33). Accordingly, CAS9-D10A induces single strand nicks rather than DSBs (32, 33), although certainly such nicks could be processed into DSBs within the cell. The reduced second-strand cleavage of CAS9-D10A should be less proficient at inducing end-joining (EJ) versus HR, as compared to CAS9-WT, or I-Scel.

Figure 1A:
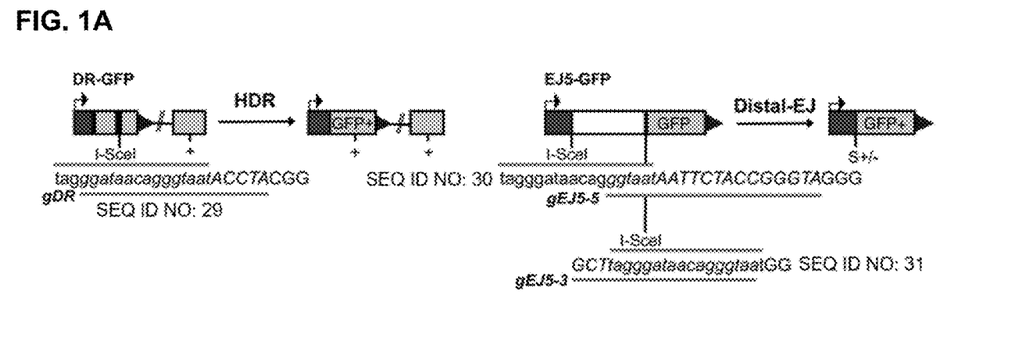
FIGS. 1A-C illustrate induction of chromosomal breaks by distinct nucleases to examine HR and EJ, according to one embodiment.
Figure 1B:
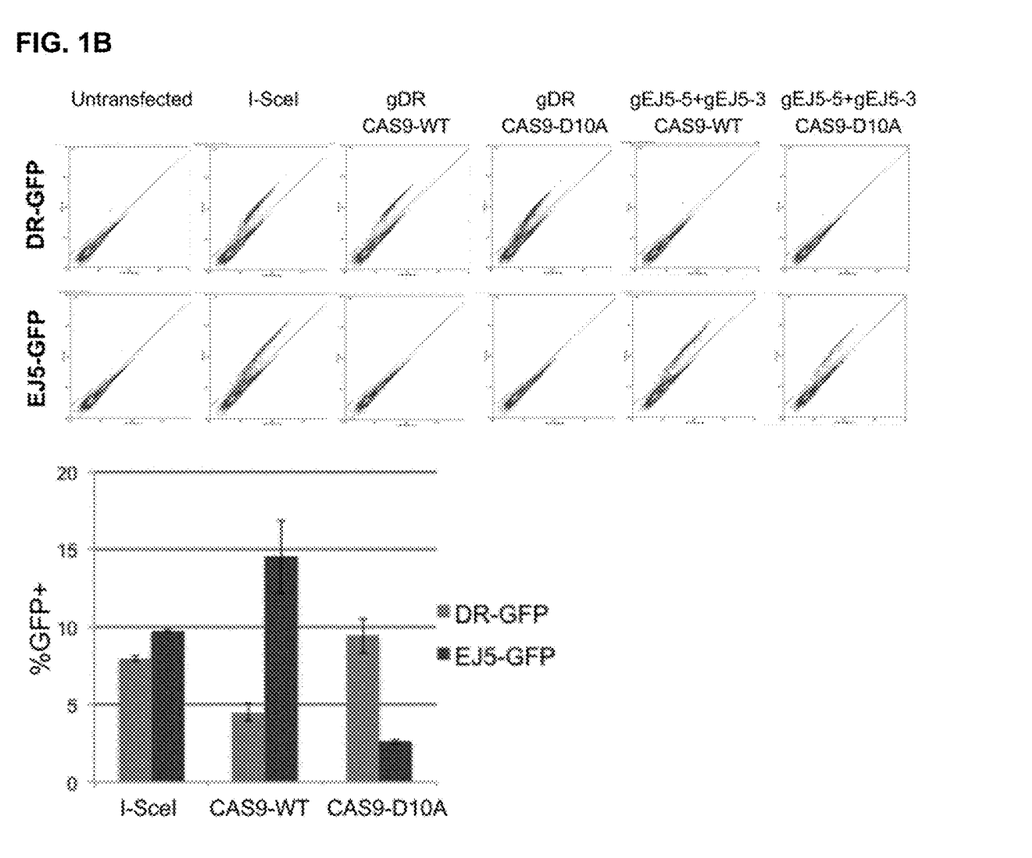

To test this, the relative efficiency of CAS9-WT and CAS9-D10A was evaluated to induce HR versus EJ, using previously described reporter systems integrated into U2OS human cells (27). For HR, the DR-GFP reporter was used, which is designed to measure a RAD51-dependent subtype of HR, homology-directed repair (HDR). DR-GFP contains a GFP expression cassette that is interrupted by an I-Scel recognition site, followed 3' by an internal GFP fragment, which if used as a template for HDR, restores the GFP+ cassette (34). For EJ, the EJ5-GFP reporter was used, which contains two segments of a GFP expression cassette interrupted by a puro gene that is flanked by two I-Scel recognition sites (35). EJ that uses the distal ends of two tandem I-Scel-induced DSBs (Distal-EJ) restores the GFP expression cassette (35). A set of gRNAs that target a portion of the I-Scel recognition site in each reporter was designed along with unique flanking sequence. Accordingly, gDR is designed to target the I-Scel site in DR-GFP, while gEJ5-5 and gEJ5-3 target the 5' and 3' I-Scel sites in EJ5-GFP, respectively (FIG. 1A). Consistent with the sequence specificity of the gRNAs to direct CAS9 chromosomal breaks, expression of CAS9-WT with gDR, but not gEJ5-5/gEJ5-3, induced the GFP+ HDR product in the DR-GFP reporter; and expression of CAS9-WT with gEJ5-5/gEJ5-3, but not gDR, induced the GFP+ Distal-EJ product in EJ5-GFP (FIG. 1B). Using these reagents, the relative efficiency of each nuclease at inducing HDR versus Distal-EJ was compared. It was found that I-SceI expression induced HDR slightly less than Distal-EJ (20% lower), CAS9-WT expression induced HDR significantly less than Distal-EJ (3-fold), whereas CAS9-D10A induced HDR significantly greater EJ (>8-fold relative to CAS9-WT alone, p<0.0001), which is likely due to increased frequency of mutagenic Proximal-EJ events, as has been found with I-SceI and Trex2 (38). Sequencing analysis of individual I-SceI-resistant products from the CAS9-WT samples showed deletion mutations flanking the target cleavage site, and Trex2 expression did not cause an obvious increase in deletion size (Table 1).

TABLE 1

Figure 1C:
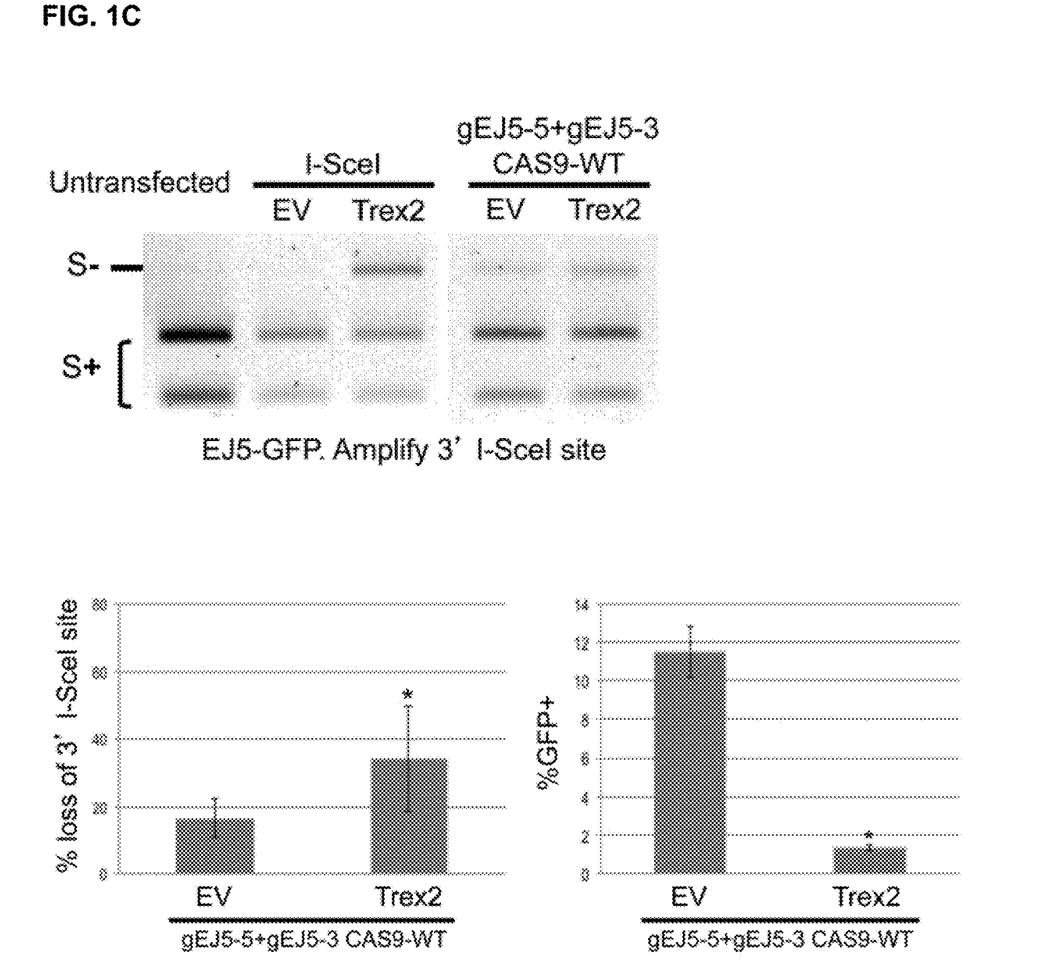

Sequences of I-SceI-resistant Proximal-EJ products amplified from the 3' SceI-site in the EJ5-GFP reporter, following the CAS9-WT and Trex2 transfections described in FIG. 1C.

| I-SceI site in capital letters./= predicted CAS9 cleavage site. (deleted nucleotides). bold = mutation | Incidence | SEQ ID NO |
|---|---|---|
| Parental sequence | | |
| agctTAGGGATAACAGGG/TAATggatc | | 7 |
| CAS9-WT junctions | | |
| agctTAGGGATAAC(A)GGG/TAATggatcc | 1/14 | 8 |
| agctTAGGGATAACAG(GG)/TAATggatcc | 1/14 | 9 |
| agctTAGGGATAACA(GGG)/TAATggatc | 4/14 | 10 |
| agctTAGGGATAACAGGG/(TAATgg)atcc | 1/14 | 11 |
| agctTAGGGATAACAGGG/(TAATGG)atcc | 1/14 | 12 |
| agctTA(GGGATAACAGGG/TA)Atggatcc | 2/14 | 13 |
| agctTAGGGACAA(CAGGG/TAATggatcc)ac | 1/14 | 14 |
| ag(c)tTA(GGGATAACAGGG/TAATg)gatcc | 1/14 | 15 |
| agctA(AGGGATAACAGGG/TAATg)gatcc | 1/14 | 16 |
| cca(tcagaagctTAGGG/ATAACAGGGTAATggatcca)ccggt | 1/14 | 17 |
| CAS9-WT + Trex2 junctions | | |
| agctTAGGGATAACAG(GG/)TAATggatcc | 1/11 | 18 |
| agctTAGGGATAACAGGG/(TAATgg)atcc | 1/11 | 19 |
| agctTAGGGATAAC(AGGG/TAA)Tggatcc | 1/11 | 20 |
| agctTAGGGATAAC(AGGG/TAAT)ggatcc | 1/11 | 21 |
| agctTAGGGA(TAACAGGG/)TAATggatcc | 1/11 | 22 |
| agctTAGGG(ATAACAGGG/T)AATggatcc | 1/11 | 23 |
| agctT(AGGGATAACAGGG/)TAATggatcc | 1/11 | 24 |
| agctTA(GGGATAACAGGG/TA)Atggatcc | 1/11 | 25 |
| agctTAGG(GATAACAGGG/TAATgg)atcc | 1/11 | 26 |
| ttttg(54nt)tcgccgccat | 1/11 | 27 |
| ttcta(56nt)gtgagc | 1/11 | 28 | than Distal-EJ (3.7-fold). This latter finding is consistent with the notion that CAS9-D10A is deficient at second-strand cleavage, since HDR is likely induced by both DSBs and single strand nicks (32, 33), whereas Distal-EJ is likely more dependent on DSBs. Although, the readily detectable level of Distal-EJ in this experiment indicates that CAS9-D10A-induced nicks may be processed into DSBs, albeit at a relatively low frequency, which has been proposed in previous reports (32, 36, 37).

Given that CAS9-WT showed a bias for inducing Distal-EJ vs. HDR, compared to I-SceI, the DSBs induced by CAS9-WT may be more prone to mutagenic EJ, thereby causing less HDR. To test this, the frequency of loss of the I-SceI site resulting from EJ that retains proximal DSB ends (Proximal-EJ) of the 3' I-SceI site in EJ5-GFP was quantified using PCR and I-SceI digestion analysis. As described previously, expression of I-SceI alone causes an undetectable level of I-SceI-resistant Proximal-EJ products, whereas co-expression of I-SceI and the 3' exonuclease Trex2 causes a substantial level of such products (38) (FIG. 1C). In contrast, CAS9-WT expression alone causes significant loss of the I-SceI site during Proximal-EJ (17±6%, FIG. 1C), which is enhanced by co-expression of the Trex2 exonuclease (2-fold, p<0.03, FIG. 1C). Furthermore, co-expression of Trex2 with CAS9-WT causes a reduction in Distal- Thus, DSBs induced by CAS9-WT appear more prone to repair via mutagenic EJ, compared to I-SceI, but such mutagenic EJ is nevertheless enhanced with co-expression of Trex2. In summary, the inducing nuclease (I-SceI, CAS9-WT, and CAS9-D10A) affects the relative frequency of distinct repair outcomes. Specifically, CAS9-WT was determined to be more efficient at inducing mutagenic EJ (i.e., NHEJ events) than HDR as compared to I-SceI, and expression of the nonprocessive exonuclease Trex2 further increases the frequency of mutagenic EJ when coexpressed with CAS9, while also limiting deletion rearrangements caused by Distal-EJ between two DSBs.

REFERENCES

The references, patents and published patent applications listed below, and all references cited in the specification above are hereby incorporated by reference in their entirety, as if fully set forth herein.

1. Stewart, G. S., Stankovic, T., Byrd, P. J., Wechsler, T., Miller, E. S., Huissoon, A., Drayson, M. T., West, S. C., Elledge, S. J. and Taylor, A. M. (2007) RIDDLE immunodeficiency syndrome is linked to defects in 53BP1-mediated DNA damage signaling. Proc Natl Acad Sci USA, 104, 16910-16915.

2. Bohgaki, T., Bohgaki, M., Cardoso, R., Panier, S., Zeegers, D., Li, L., Stewart, G. S., Sanchez, O., Hande, M. P., Durocher, D. et al. (2011) Genomic instability, defective spermatogenesis, immunodeficiency, and cancer in a mouse model of the RIDDLE syndrome. *PLoS Genet*, 7, e1001381.
3. Devgan, S. S., Sanal, O., Doil, C., Nakamura, K., Nahas, S. A., Pettijohn, K., Bartek, J., Lukas, C., Lukas, J. and Gatti, R. A. (2011) Homozygous deficiency of ubiquitin-ligase ring-finger protein RNF168 mimics the radiosensitivity syndrome of ataxia-telangiectasia. *Cell Death Differ*, 18, 1500-1506.
4. Pinato, S., Scandiuzzi, C., Arnaudo, N., Citterio, E., Gaudino, G. and Penengo, L. (2009) RNF168, a new RING finger, MIU-containing protein that modifies chromatin by ubiquitination of histones H2A and H2AX. *BMC Mol Biol*, 10, 55.
5. Doil, C., Mailand, N., Bekker-Jensen, S., Menard, P., Larsen, D. H., Pepperkok, R., Ellenberg, J., Panier, S., Durocher, D., Bartek, J. et al. (2009) RNF168 binds and amplifies ubiquitin conjugates on damaged chromosomes to allow accumulation of repair proteins. *Cell*, 136, 435-446.
6. Stewart, G. S., Panier, S., Townsend, K., Al-Hakim, A. K., Kolas, N. K., Miller, E. S., Nakada, S., Ylanko, J., Olivarius, S., Mendez, M. et al. (2009) The RIDDLE syndrome protein mediates a ubiquitin-dependent signaling cascade at sites of DNA damage. *Cell*, 136, 420-434.
7. Ward, I. M., Reina-San-Martin, B., Olaru, A., Minn, K., Tamada, K., Lau, J. S., Cascalho, M., Chen, L., Nussenzweig, A., Livak, F. et al. (2004) 53BP1 is required for class switch recombination. *J Cell Biol*, 165, 459-464.
8. Munoz, M. C., Laulier, C., Gunn, A., Cheng, A., Robbiani, D. F., Nussenzweig, A. and Stark, J. M. (2012) RING finger nuclear factor RNF168 is important for defects in homologous recombination caused by loss of the breast cancer susceptibility factor BRCA1. *J Biol Chem*, 287, 40618-40628.
9. Bunting, S. F., Callen, E., Wong, N., Chen, H. T., Polato, F., Gunn, A., Bothmer, A., Feldhahn, N., Fernandez-Capetillo, O., Cao, L. et al. (2010) 53BP1 inhibits homologous recombination in Brca1-deficient cells by blocking resection of DNA breaks. *Cell*, 141, 243-254.
10. Bouwman, P., Aly, A., Escandell, J. M., Pieterse, M., Bartkova, J., van der Gulden, H., Hiddingh, S., Thanasoula, M., Kulkarni, A., Yang, Q. et al. (2010) 53BP1 loss rescues BRCA1 deficiency and is associated with triple-negative and BRCA-mutated breast cancers. *Nat Struct Mol Biol*, 17, 688-695.
11. Mattiroli, F., Vissers, J. H., van Dijk, W. J., Ikpa, P., Citterio, E., Vermeulen, W., Marteijn, J. A. and Sixma, T. K. (2012) RNF168 ubiquitinates K13-15 on H2A/H2AX to drive DNA damage signaling. *Cell*, 150, 1182-1195.
12. Gatti, M., Pinato, S., Maspero, E., Soffientini, P., Polo, S. and Penengo, L. (2012) A novel ubiquitin mark at the N-terminal tail of histone H2As targeted by RNF168 ubiquitin ligase. *Cell Cycle*, 11, 2538-2544.
13. Fradet-Turcotte, A., Canny, M. D., Escribano-Diaz, C., Orthwein, A., Leung, C. C., Huang, H., Landry, M. C., Kitevski-LeBlanc, J., Noordermeer, S. M., Sicheri, F. et al. (2013) 53BP1 is a reader of the DNA-damage-induced H2A Lys 15 ubiquitin mark. *Nature*, 499, 50-54.
14. Huen, M. S., Grant, R., Manke, I., Minn, K., Yu, X., Yaffe, M. B. and Chen, J. (2007) RNF8 transduces the DNA-damage signal via histone ubiquitylation and checkpoint protein assembly. *Cell*, 131, 901-914.
15. Kolas, N. K., Chapman, J. R., Nakada, S., Ylanko, J., Chahwan, R., Sweeney, F. D., Panier, S., Mendez, M., Wildenhain, J., Thomson, T. M. et al. (2007) Orchestration of the DNA-damage response by the RNF8 ubiquitin ligase. *Science*, 318, 1637-1640.
16. Mailand, N., Bekker-Jensen, S., Faustrup, H., Melander, F., Bartek, J., Lukas, C. and Lukas, J. (2007) RNF8 ubiquitylates histones at DNA double-strand breaks and promotes assembly of repair proteins. *Cell*, 131, 887-900.
17. Wang, B. and Elledge, S. J. (2007) Ubc13/Rnf8 ubiquitin ligases control foci formation of the Rap80/Abraxas/Brca1/Brcc36 complex in response to DNA damage. *Proc Natl Acad Sci USA*, 104, 20759-20763.
18. Panier, S., Ichijima, Y., Fradet-Turcotte, A., Leung, C. C., Kaustov, L., Arrowsmith, C. H. and Durocher, D. (2012) Tandem protein interaction modules organize the ubiquitin-dependent response to DNA double-strand breaks. *Mol Cell*, 47, 383-395.
19. Gudjonsson, T., Altmeyer, M., Savic, V., Toledo, L., Dinant, C., Grofte, M., Bartkova, J., Poulsen, M., Oka, Y., Bekker-Jensen, S. et al. (2012) TRIP12 and UBR5 suppress spreading of chromatin ubiquitylation at damaged chromosomes. *Cell*, 150, 697-709.
20. Panier, S. and Durocher, D. (2013) Push back to respond better: regulatory inhibition of the DNA double-strand break response. *Nat Rev Mol Cell Biol*, 14, 661-672.
21. Evers, B., Helleday, T. and Jonkers, J. (2010) Targeting homologous recombination repair defects in cancer. *Trends Pharmacol Sci*, 31, 372-380.
22. Moynahan, M. E. and Jasin, M. (2010) Mitotic homologous recombination maintains genomic stability and suppresses tumorigenesis. *Nat Rev Mol Cell Biol*, 11, 196-207.
23. TCGA. (2011) Integrated genomic analyses of ovarian carcinoma. *Nature*, 474, 609-615.
24. Kass, E. M., Moynahan, M. E. and Jasin, M. (2010) Loss of 53BP1 is a gain for BRCA1 mutant cells. *Cancer Cell*, 17, 423-425.
25. Pinato, S., Gatti, M., Scandiuzzi, C., Confalonieri, S. and Penengo, L. (2011) UMI, a novel RNF168 ubiquitin binding domain involved in the DNA damage signaling pathway. *Mol Cell Biol*, 31, 118-126.
26. Gunn, A., Bennardo, N., Cheng, A. and Stark, J. M. (2011) Correct End Use during End Joining of Multiple Chromosomal Double Strand Breaks Is Influenced by Repair Protein RAD50, DNA-dependent Protein Kinase DNA-PKcs, and Transcription Context. *J Biol Chem*, 286, 42470-42482.
27. Gunn, A. and Stark, J. M. (2012) I-SceI-based assays to examine distinct repair outcomes of mammalian chromosomal double strand breaks. *Methods Mol Biol*, 920, 379-391.
28. Lilley, C. E., Chaurushiya, M. S., Boutell, C., Landry, S., Suh, J., Panier, S., Everett, R. D., Stewart, G. S., Durocher, D. and Weitzman, M. D. (2010) A viral E3 ligase targets RNF8 and RNF168 to control histone ubiquitination and DNA damage responses. *Embo J*, 29, 943-955.
29. Xie, A., Puget, N., Shim, I., Odate, S., Jarzyna, I., Bassing, C. H., Alt, F. W. and Scully, R. (2004) Control of sister chromatid recombination by histone H2AX. *Mol Cell*, 16, 1017-1025.
30. Cong, L., Ran, F. A., Cox, D., Lin, S., Barretto, R., Habib, N., Hsu, P. D., Wu, X., Jiang, W., Marraffini, L. A. et al. (2013) Multiplex genome engineering using CRISPR/Cas systems. *Science*, 339, 819-823.
31. Moure, C. M., Gimble, F. S. and Quiocho, F. A. (2003) The crystal structure of the gene targeting homing endonuclease I-SceI reveals the origins of its target site specificity. *J Mol Biol*, 334, 685-695.
32. Ran, F. A., Hsu, P. D., Wright, J., Agarwala, V., Scott, D. A. and Zhang, F. (2013) Genome engineering using the CRISPR-Cas9 system. *Nat Protoc*, 8, 2281-2308.
33. Jinek, M., Chylinski, K., Fonfara, I., Hauer, M., Doudna, J. A. and Charpentier, E. (2012) A programmable dual-RNA-guided DNA endonuclease in adaptive bacterial imm unity. *Science*, 337, 816-821.
34. Pierce, A. J., Johnson, R. D., Thompson, L. H. and Jasin, M. (1999) XRCC3 promotes homology-directed repair of DNA damage in mammalian cells. *Genes Dev*, 13, 2633-2638.
35. Bennardo, N., Cheng, A., Huang, N. and Stark, J. M. (2008) Alternative-NHEJ Is a Mechanistically Distinct Pathway of Mammalian Chromosome Break Repair. *PLoS Genet*, 4, e1000110.
36. Mali, P., Yang, L., Esvelt, K. M., Aach, J., Guell, M., DiCarlo, J. E., Norville, J. E. and Church, G. M. (2013) RNA-guided human genome engineering via Cas9. *Science*, 339, 823-826.
37. Ran, F. A., Hsu, P. D., Lin, C. Y., Gootenberg, J. S., Konermann, S., Trevino, A. E., Scott, D. A., Inoue, A., Matoba, S., Zhang, Y. et al. (2013) Double nicking by RNA-guided CRISPR Cas9 for enhanced genome editing specificity. *Cell*, 154, 1380-1389.
38. Bennardo, N., Gunn, A., Cheng, A., Hasty, P. and Stark, J. M. (2009) Limiting the persistence of a chromosome break diminishes its mutagenic potential. *PLoS Genet*, 5, e1000683.
39. Stark, J. M., Pierce, A. J., Oh, J., Pastink, A. and Jasin, M. (2004) Genetic steps of mammalian homologous repair with distinct mutagenic consequences. *Mol Cell Biol*, 24, 9305-9316.
40. Sy, S. M., Jiang, J., Dong, S. S., Lok, G. T., Wu, J., Cai, H., Yeung, E. S., Huang, J., Chen, J., Deng, Y. et al. (2011) Critical roles of ring finger protein RNF8 in replication stress responses. *J Biol Chem*, 286, 22355-22361.
41. Huang, J., Huen, M. S., Kim, H., Leung, C. C., Glover, J. N., Yu, X. and Chen, J. (2009) RAD18 transmits DNA damage signalling to elicit homologous recombination repair. *Nat Cell Biol*, 11, 592-603.
42. Santos, M. A., Huen, M. S., Jankovic, M., Chen, H. T., Lopez-Contreras, A. J., Klein, I. A., Wong, N., Barbancho, J. L., Fernandez-Capetillo, O., Nussenzweig, M. C. et al. (2010) Class switching and meiotic defects in mice lacking the E3 ubiquitin ligase RNF8. *J Exp Med*, 207, 973-981.
43. Nakada, S., Yonamine, R. M. and Matsuo, K. (2012) RNF8 regulates assembly of RAD51 at DNA double-strand breaks in the absence of BRCA1 and 53BP1. *Cancer Res*, 72, 4974-4983.
44. Kim, H. and D'Andrea, A. D. (2012) Regulation of DNA cross-link repair by the Fanconi anemia/BRCA pathway. *Genes Dev*, 26, 1393-1408.
45. Nakanishi, K., Yang, Y. G., Pierce, A. J., Taniguchi, T., Digweed, M., D'Andrea, A. D., Wang, Z. Q. and Jasin, M. (2005) Human Fanconi anemia monoubiquitination pathway promotes homologous DNA repair. *Proc Natl Acad Sci USA*, 102, 1110-1115.
46. Leung, J. W., Agarwal, P., Canny, M. D., Gong, F., Robison, A. D., Finkelstein, I. J., Durocher, D. and Miller, K. M. (2014) Nucleosome Acidic Patch Promotes RNF168- and RING1B/BMI1-Dependent H2AX and H2A Ubiquitination and DNA Damage Signaling. *PLoS Genet*, 10, e1004178.
47. Mattiroli, F., Uckelmann, M., Sahtoe, D. D., van Dijk, W. J. and Sixma, T. K. (2014) The nucleosome acidic patch plays a critical role in RNF168-dependent ubiquitination of histone H2A. *Nat Commun*, 5, 3291.
48. Kinner, A., Wu, W., Staudt, C. and Iliakis, G. (2008) Gamma-H2AX in recognition and signaling of DNA double-strand breaks in the context of chromatin. *Nucleic Acids Res*, 36, 5678-5694.
49. Soutoglou, E. and Misteli, T. (2008) Activation of the cellular DNA damage response in the absence of DNA lesions. *Science*, 320, 1507-1510.
50. Lukas, J., Lukas, C. and Bartek, J. (2011) More than just a focus: The chromatin response to DNA damage and its role in genome integrity maintenance. *Nat Cell Biol*, 13, 1161-1169.
51. Shanbhag, N. M., Rafalska-Metcalf, I. U., Balane-Bolivar, C., Janicki, S. M. and Greenberg, R. A. (2010) ATM-dependent chromatin changes silence transcription in cis to DNA double-strand breaks. *Cell*, 141, 970-981.
52. Ramachandran, S., Chahwan, R., Nepal, R. M., Frieder, D., Panier, S., Roa, S., Zaheen, A., Durocher, D., Scharff, M. D. and Martin, A. (2010) The RNF8/RNF168 ubiquitin ligase cascade facilitates class switch recombination. *Proc Natl Acad Sci USA*, 107, 809-814.
53. Yan, Z., Guo, R., Paramasivam, M., Shen, W., Ling, C., Fox, D., 3rd, Wang, Y., Oostra, A. B., Kuehl, J., Lee, D. Y. et al. (2012) A ubiquitin-binding protein, FAAP20, links RNF8-mediated ubiquitination to the Fanconi anemia DNA repair network. *Mol Cell*, 47, 61-75.
54. Certo, M. T., Gwiazda, K. S., Kuhar, R., Sather, B., Curinga, G., Mandt, T., Brault, M., Lambert, A. R., Baxter, S. K., Jacoby, K. et al. (2012) Coupling endonucleases with DNA end-processing enzymes to drive gene disruption. *Nat Methods*, 9, 973-975.

What is claimed is:

1. A composition comprising:
   a first expression cassette comprising a nucleotide sequence which encodes a CAS9 endonuclease, wherein the CAS9 endonuclease generates blunt ended double strand breaks;
   a second expression cassette comprising a nucleotide sequence which encodes a guide RNA sequence, wherein the guide RNA sequence is complementary to a target genome nucleotide sequence in a cell; and
   a third expression cassette comprising a nucleotide sequence which encodes a Trex2 exonuclease (Trex2) gene;
   wherein the first, second, and third expression cassettes comprise a portion of one or more expression vectors.

2. The composition of claim 1, wherein the first and second expression cassettes comprise a portion of a first expression vector and the third expression cassette comprises a portion of a second expression vector.

3. The composition of claim 1, wherein the first, second, and third expression cassettes comprise a portion of a single expression vector.

4. The composition of claim 1, wherein the one or more expression vectors is a plasmid.

5. The composition of claim 1, wherein the one or more expression vectors is a recombinant viral vector selected from a recombinant adeno-associated virus (AAV), adenovirus, lentivirus, or baculovirus.

6. An isolated cell comprising one or more expression vectors encoding:
- a CAS9 endonuclease, wherein the CAS9 endonuclease generates blunt ended double strand breaks;
- a guide RNA sequence, wherein the guide RNA sequence is complementary to a target genomic nucleotide sequence; and
- a Trex2 exonuclease.

7. The isolated cell of claim 6, wherein the CAS9 endonuclease is capable of causing a disruption of the target genomic nucleotide sequence when expressed in the cell.

8. The isolated cell of claim 7, wherein the disruption is an insertion or deletion of one or more nucleotides within the target genomic nucleotide sequence.

9. The isolated cell of claim 6, wherein a first expression cassette comprising a nucleotide sequence encoding the CAS9 endonuclease and a second expression cassette comprising a nucleotide sequence encoding the guide RNA sequence further comprise a portion of a first expression vector and the third expression cassette comprising a nucleotide sequence encoding the Trex2 exonuclease further comprises a portion of a second expression vector.

10. The isolated cell of claim 6, wherein the first, second, and third expression cassettes comprise a portion of a single expression vector.

11. The isolated cell of claim 6, wherein the one or more expression vectors is a plasmid.

12. The isolated cell of claim 6, wherein the one or more expression vectors is a recombinant viral vector selected from a recombinant AAV, adenovirus, lentivirus, or baculovirus.

* * * * *

SEQUENCE LISTING

<160> NUMBER OF SEQ ID NOS: 31

<210> SEQ ID NO 1
<211> LENGTH: 3
<212> TYPE: RNA
<213> ORGANISM: Artificial Sequence
<220> FEATURE:
<223> OTHER INFORMATION: protospacer adjacent motif derived from S. pyogenes
<220> FEATURE:
<221> NAME/KEY: misc_feature
<222> LOCATION: (1)..(1)
<223> OTHER INFORMATION: n is a, c, g, or u

<400> SEQUENCE: 1

```
ngg                                                                 3

<210> SEQ ID NO 2
<211> LENGTH: 6
<212> TYPE: RNA
<213> ORGANISM: Artificial Sequence
<220> FEATURE:
<223> OTHER INFORMATION: protospacer adjacent motif derived from N.
      meningitides
<220> FEATURE:
<221> NAME/KEY: misc_feature
<222> LOCATION: (1)..(4)
<223> OTHER INFORMATION: n is a, c, g, or u

<400> SEQUENCE: 2 nnnnga                                                              6

<210> SEQ ID NO 3
<211> LENGTH: 6
<212> TYPE: RNA
<213> ORGANISM: Artificial Sequence
<220> FEATURE:
<223> OTHER INFORMATION: protospacer adjacent motif derived from S.
      thermophiles
<220> FEATURE:
<221> NAME/KEY: misc_feature
<222> LOCATION: (1)..(2)
<223> OTHER INFORMATION: n is a, c, g, or u

<400> SEQUENCE: 3 nnagaa                                                              6

<210> SEQ ID NO 4
<211> LENGTH: 6
<212> TYPE: RNA
<213> ORGANISM: Artificial Sequence
<220> FEATURE:
<223> OTHER INFORMATION: protospacer adjacent motif derived from T.
      denticola
<220> FEATURE:
<221> NAME/KEY: misc_feature
<222> LOCATION: (1)..(1)
<223> OTHER INFORMATION: n is a, c, g, or u

<400> SEQUENCE: 4 naaaac                                                              6

<210> SEQ ID NO 5
<211> LENGTH: 20
<212> TYPE: DNA
<213> ORGANISM: Artificial Sequence
<220> FEATURE:
<223> OTHER INFORMATION: primer

<400> SEQUENCE: 5
cagctctagg cctcattgtt                                              20

<210> SEQ ID NO 6
<211> LENGTH: 20
<212> TYPE: DNA
<213> ORGANISM: Artificial Sequence
<220> FEATURE:
<223> OTHER INFORMATION: primer

<400> SEQUENCE: 6
agagcctgga tgaatggatg                                              20
```

```
<210> SEQ ID NO 7
<211> LENGTH: 27
<212> TYPE: DNA
<213> ORGANISM: Artificial Sequence
<220> FEATURE:
<223> OTHER INFORMATION: I-SceI-resistant proximal-EJ

<400> SEQUENCE: 7
agcttaggga taacagggta atggatc                                              27

<210> SEQ ID NO 8
<211> LENGTH: 27
<212> TYPE: DNA
<213> ORGANISM: Artificial Sequence
<220> FEATURE:
<223> OTHER INFORMATION: CAS99-WT junction

<400> SEQUENCE: 8
agcttaggga taacgggtaa tggatcc                                              27

<210> SEQ ID NO 9
<211> LENGTH: 26
<212> TYPE: DNA
<213> ORGANISM: Artificial Sequence
<220> FEATURE:
<223> OTHER INFORMATION: CAS9-WT junction

<400> SEQUENCE: 9
agcttaggga taacagtaat ggatcc                                               26

<210> SEQ ID NO 10
<211> LENGTH: 24
<212> TYPE: DNA
<213> ORGANISM: Artificial Sequence
<220> FEATURE:
<223> OTHER INFORMATION: CAS9-WT junction

<400> SEQUENCE: 10
agcttaggga taacataatg gatc                                                 24

<210> SEQ ID NO 11
<211> LENGTH: 22
<212> TYPE: DNA
<213> ORGANISM: Artificial Sequence
<220> FEATURE:
<223> OTHER INFORMATION: CAS9-WT junction

<400> SEQUENCE: 11
agcttaggga taacagggat cc                                                   22

<210> SEQ ID NO 12
<211> LENGTH: 22
<212> TYPE: DNA
<213> ORGANISM: Artificial Sequence
<220> FEATURE:
<223> OTHER INFORMATION: CAS9-WT junction

<400> SEQUENCE: 12
agcttaggga taacagggat cc                                                   22

<210> SEQ ID NO 13
<211> LENGTH: 14
<212> TYPE: DNA
<213> ORGANISM: Artificial Sequence
<220> FEATURE:
<223> OTHER INFORMATION: CAS9-WT junction
```

```
<400> SEQUENCE: 13
agcttaatgg atcc                                                          14

<210> SEQ ID NO 14
<211> LENGTH: 15
<212> TYPE: DNA
<213> ORGANISM: Artificial Sequence
<220> FEATURE:
<223> OTHER INFORMATION: CAS9-WT junction

<400> SEQUENCE: 14
agcttaggga caaac                                                         15

<210> SEQ ID NO 15
<211> LENGTH: 10
<212> TYPE: DNA
<213> ORGANISM: Artificial Sequence
<220> FEATURE:
<223> OTHER INFORMATION: CAS9-WT junction

<400> SEQUENCE: 15
agttagatcc                                                               10

<210> SEQ ID NO 16
<211> LENGTH: 10
<212> TYPE: DNA
<213> ORGANISM: Artificial Sequence
<220> FEATURE:
<223> OTHER INFORMATION: CAS9-WT junction

<400> SEQUENCE: 16
agctagatcc                                                               10

<210> SEQ ID NO 17
<211> LENGTH: 8
<212> TYPE: DNA
<213> ORGANISM: Artificial Sequence
<220> FEATURE:
<223> OTHER INFORMATION: CAS9-WT junction

<400> SEQUENCE: 17 ccaccggt                                                                  8

<210> SEQ ID NO 18
<211> LENGTH: 26
<212> TYPE: DNA
<213> ORGANISM: Artificial Sequence
<220> FEATURE:
<223> OTHER INFORMATION: CAS9-WT and Trex2 junction

<400> SEQUENCE: 18
agcttaggga taacagtaat ggatcc                                             26

<210> SEQ ID NO 19
<211> LENGTH: 22
<212> TYPE: DNA
<213> ORGANISM: Artificial Sequence
<220> FEATURE:
<223> OTHER INFORMATION: CAS9-WT and Trex2 junction

<400> SEQUENCE: 19
agcttaggga taacagggat cc                                                 22

<210> SEQ ID NO 20
<211> LENGTH: 21
```

```
<212> TYPE: DNA
<213> ORGANISM: Artificial Sequence
<220> FEATURE:
<223> OTHER INFORMATION: CAS9-WT and Trex2 junction

<400> SEQUENCE: 20
agcttaggga taactggatc c                                              21

<210> SEQ ID NO 21
<211> LENGTH: 20
<212> TYPE: DNA
<213> ORGANISM: Artificial Sequence
<220> FEATURE:
<223> OTHER INFORMATION: CAS9-WT and Trex2 junction

<400> SEQUENCE: 21
agcttaggga taacggatcc                                                20

<210> SEQ ID NO 22
<211> LENGTH: 20
<212> TYPE: DNA
<213> ORGANISM: Artificial Sequence
<220> FEATURE:
<223> OTHER INFORMATION: CAS9-WT and Trex2 junction

<400> SEQUENCE: 22
agcttaggga taatggatcc                                                20

<210> SEQ ID NO 23
<211> LENGTH: 18
<212> TYPE: DNA
<213> ORGANISM: Artificial Sequence
<220> FEATURE:
<223> OTHER INFORMATION: CAS9-WT and Trex2 junction

<400> SEQUENCE: 23
agcttaggga atggatcc                                                  18

<210> SEQ ID NO 24
<211> LENGTH: 15
<212> TYPE: DNA
<213> ORGANISM: Artificial Sequence
<220> FEATURE:
<223> OTHER INFORMATION: CAS9-WT and Trex2 junction

<400> SEQUENCE: 24
agctttaatg gatcc                                                     15

<210> SEQ ID NO 25
<211> LENGTH: 14
<212> TYPE: DNA
<213> ORGANISM: Artificial Sequence
<220> FEATURE:
<223> OTHER INFORMATION: CAS9-WT and Trex2 junction

<400> SEQUENCE: 25
agcttaatgg atcc                                                      14

<210> SEQ ID NO 26
<211> LENGTH: 12
<212> TYPE: DNA
<213> ORGANISM: Artificial Sequence
<220> FEATURE:
<223> OTHER INFORMATION: CAS9-WT and Trex2 junction

<400> SEQUENCE: 26
```

```
agcttaggat cc                                                          12

<210> SEQ ID NO 27
<211> LENGTH: 15
<212> TYPE: DNA
<213> ORGANISM: Artificial Sequence
<220> FEATURE:
<223> OTHER INFORMATION: CAS9-WT and Trex2 junction

<400> SEQUENCE: 27
ttttgtcgcc gccat                                                       15

<210> SEQ ID NO 28
<211> LENGTH: 11
<212> TYPE: DNA
<213> ORGANISM: Artificial Sequence
<220> FEATURE:
<223> OTHER INFORMATION: CAS9-WT and Trex2 junction

<400> SEQUENCE: 28
ttctagtgag c                                                           11

<210> SEQ ID NO 29
<211> LENGTH: 26
<212> TYPE: DNA
<213> ORGANISM: Artificial Sequence
<220> FEATURE:
<223> OTHER INFORMATION: guide RNA targeting sequence

<400> SEQUENCE: 29
tagggataac agggtaatac ctacgg                                           26

<210> SEQ ID NO 30
<211> LENGTH: 35
<212> TYPE: DNA
<213> ORGANISM: Artificial Sequence
<220> FEATURE:
<223> OTHER INFORMATION: guide RNA targeting sequence

<400> SEQUENCE: 30
tagggataac agggtaataa ttctaccggg taggg                                 35

<210> SEQ ID NO 31
<211> LENGTH: 23
<212> TYPE: DNA
<213> ORGANISM: Artificial Sequence
<220> FEATURE:
<223> OTHER INFORMATION: guide RNA targeting sequence

<400> SEQUENCE: 31
gcttagggat aacagggtaa tgg                                              23
```

UNITED STATES PATENT AND TRADEMARK OFFICE
CERTIFICATE OF CORRECTION

| | |
|---|---|
| PATENT NO. | : 11,427,819 B2 |
| APPLICATION NO. | : 16/210337 |
| DATED | : August 30, 2022 |
| INVENTOR(S) | : Jeremy M. Stark et al. |

Page 1 of 1

It is certified that error appears in the above-identified patent and that said Letters Patent is hereby corrected as shown below:

In the Specification

Statement of Government Interest section, Column 1, Lines 14-18, please delete:
"The present invention was made with government support under Grant Nos. R01CA120954 and P30CA33572, awarded by the National Cancer Institute of the National Institutes of Health. The government has certain rights in the invention."

And insert:
--This invention was made with government support under P30 CA033572, and R01 CA120954 awarded by the National Institutes of Health. The government has certain rights in the invention.--

Signed and Sealed this
Ninth Day of September, 2025

Coke Morgan Stewart
*Acting Director of the United States Patent and Trademark Office*